US012780864B2

(12) United States Patent
Du et al.

(10) Patent No.: US 12,780,864 B2
(45) Date of Patent: Nov. 3, 2026

(54) METHOD FOR PREPARING STACHYOSE

(71) Applicant: SHANDONG BAILONG CHUANGYUAN BIO-TECH CO., LTD, Shandong (CN)

(72) Inventors: Qian Du, Shandong (CN); Lingling Chen, Shandong (CN); Jianjin Dong, Shandong (CN); Xianbao Shao, Shandong (CN); Guoqing Liu, Shandong (CN)

(73) Assignee: SHANDONG BAILONG CHUANGYUAN BIO-TECH CO., LTD, Shandong (CN)

( * ) Notice: Subject to any disclaimer, the term of this patent is extended or adjusted under 35 U.S.C. 154(b) by 344 days.

(21) Appl. No.: 18/724,151

(22) PCT Filed: Dec. 27, 2022

(86) PCT No.: PCT/CN2022/142234
§ 371 (c)(1),
(2) Date: Jun. 25, 2024

(87) PCT Pub. No.: WO2023/125505
PCT Pub. Date: Jul. 6, 2023

(65) Prior Publication Data

US 2025/0059225 A1 Feb. 20, 2025

(30) Foreign Application Priority Data

Dec. 29, 2021 (CN) ......................... 202111633962.7

(51) Int. Cl.
*C07H 3/06* (2006.01)
*C07H 1/08* (2006.01)

(52) U.S. Cl.
CPC ................. *C07H 3/06* (2013.01); *C07H 1/08* (2013.01)

(58) Field of Classification Search
None
See application file for complete search history.

(56) References Cited

U.S. PATENT DOCUMENTS

2018/0092394 A1* 4/2018 Shen ....................... A23P 10/40

FOREIGN PATENT DOCUMENTS

| | | | |
|---|---|---|---|
| CN | 101003551 | A | 7/2007 |
| CN | 101538291 | A | 9/2009 |
| CN | 101633676 | A | 1/2010 |
| CN | 105017339 | A | 11/2015 |
| CN | 109694393 | A | 4/2019 |
| CN | 110759956 | A | 2/2020 |
| CN | 110903329 | A | 3/2020 |
| CN | 112175024 | A | 1/2021 |
| CN | 114213475 | A | 3/2022 |
| JP | H07-82287 | A | 3/1995 |

OTHER PUBLICATIONS

First Office Action and search report mailed Sep. 5, 2022, in the Chinese Patent Application No. 202111633962.7. English translation and original Chinese language versions. 19 pages.
International Search Report and Written Opinion mailed Mar. 21, 2023, in the International patent application No. PCT/CN2022/142234. English translation and original Chinese language versions. 17 pages.
Wu, Renfang et al., "Chapter 4: Ion Exchange Desalination," Power Plant Chemistry, third edition, Chinese Electric Power Press, Beijing, Aug. 31, 2004, sections 7 and 8, p. 81-87. English translation and original Chinese language versions. 18 pages.
Zongli, Liu et al., "Application of Simulant Moving Bed Chromatography in Production of Functional Oligosaccharides," China Academic Journal Electronic Publishing House, Mar. 2012. English Abstract only. 5 pages.

* cited by examiner

*Primary Examiner* — Dale R Miller
(74) *Attorney, Agent, or Firm* — Wilmer Cutler Pickering Hale and Dorr LLP

(57) ABSTRACT

The present disclosure provides a method for preparing stachyose, which method belongs to the technical field of the production of carbohydrates. The method includes: breaking the wall of *Stachys affinis*; subjecting the resulting wall-broken material to filter pressing to obtain a filtrate and filter residues; decoloring the filtrate to obtain a decolored liquid; filtering the decolored liquid with a nanofiltration membrane to obtain a nanofiltration liquid; subjecting the nanofiltration liquid to a mixed bed ion exchange treatment to obtain an exchanged liquid; purifying the exchanged liquid by means of continuous simulated moving bed chromatography to obtain a purified liquid; and concentrating and vacuum drying the purified liquid to obtain stachyose.

10 Claims, 1 Drawing Sheet

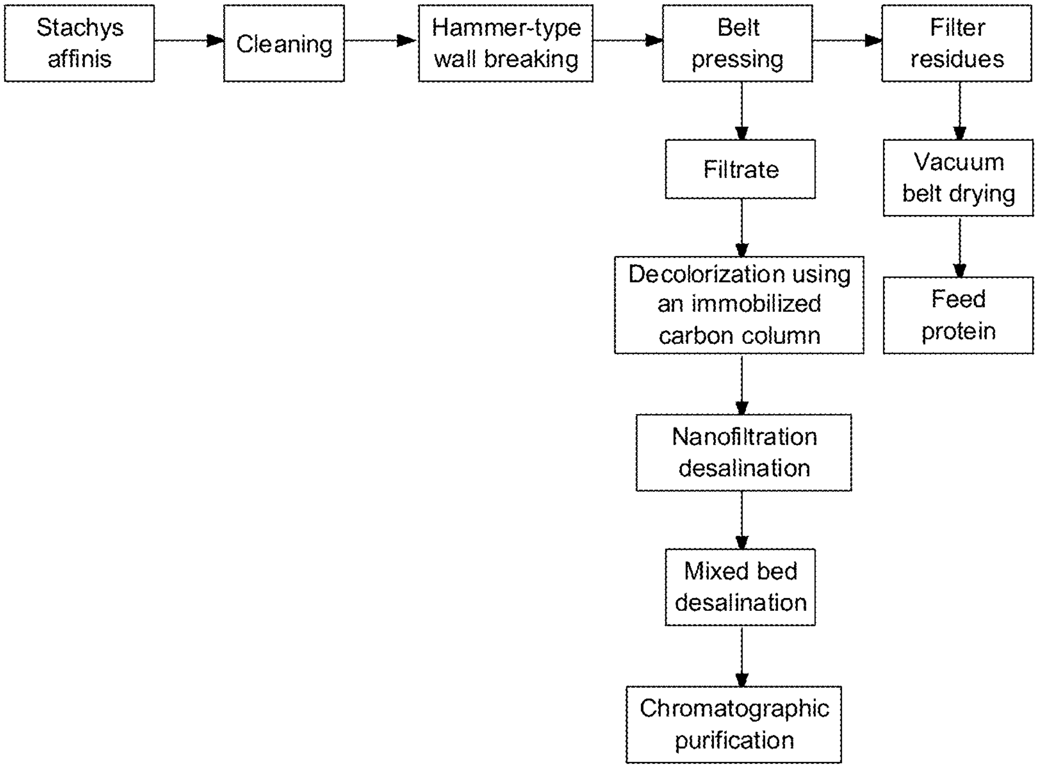
Stachys affinis
Cleaning
Hammer-type wall breaking
Belt pressing
Filter residues
Filtrate
Vacuum belt drying
Decolorization using an immobilized carbon column
Feed protein
Nanofiltration desalination
Mixed bed desalination
Chromatographic purification

METHOD FOR PREPARING STACHYOSE

CROSS-REFERENCE

This application is a 371 National Phase application which claims priority to PCT/CN2022/142234 filed Dec. 27, 2022; which claims priority to Chinese Patent Application No. 202111633962.7 filed on Dec. 29, 2021, which is incorporated by reference herein in its entirety.

TECHNICAL FIELD

The disclosure belongs to the technical field of the production of saccharides, and especially, it relates to a method for preparing Stachyose.

BACKGROUND ART

Stachyose is a tetra-saccharide that is a white powder and slightly sweet in taste. It has a molecular formula $C_{24}H_{42}O_{21}$, and a molecular structure of "galactose-galactose-glucose-fructose".

*Stachys affinis* is a plant in *Stachys* Genus, Labiatae Family. The tubers of the *Stachys affinis* is rich in Stachyose.

SUMMARY OF INVENTION

The inventors find that in traditional production and preparation technologies of Stachyose, the following problems are involved:

(1) Traditional production and preparation technologies of Stachyose is insufficient in desalinating treatment, and due to a high salt content in raw materials, the electric conductivity of a final product is high.

(2) Some traditional production and preparation technologies of Stachyose adopt a reverse osmosis membrane technology for desalinating, while the reverse osmosis membrane has a limited treatment capacity, and thus it is not applicable for large-scale industrial production.

(3) The Stachyose products obtained according to traditional production and preparation technologies of Stachyose have a low purity, about 90%-93%.

In view of this, it is the object of the present disclosure to provide a method for preparing Stachyose, and with the method provided by the present disclosure, the Stachyose product has a high purity, a low salt content and a low electrical conductivity.

In order to achieve the above object, the present disclosure provides the following technical solution:

The disclosure provides a method for preparing Stachyose, comprising the following steps:

1) breaking walls of *Stachys affinis*, to obtain a wall-broken material;

2) subjecting the wall-broken material obtained in the step 1) to filter pressing, to obtain a filtrate and filter residues;

3) subjecting the filtrate obtained in the step 2) to a decoloring treatment, to obtain a decolorized liquid;

4) subjecting the decolorized liquid obtained in the step 3) to a nanofiltration membrane filtration, to obtain a nanofiltration liquid;

conditions of the nanofiltration membrane filtration include: a molecular weight cut-off of the nanofiltration membrane of 100 Da-500 Da, a temperature of 30° C.-40° C., and a pressure of 0.35 Mpa-1 Mpa;

5) subjecting the nanofiltration liquid obtained in the step 4) to a mixed bed ion exchange treatment, to obtain an exchanged liquid;

conditions of the mixed bed ion exchange treatment include: a temperature of 20° C.-30° C., and a flow rate per hour of the nanofiltration liquid of 1.5 times-2.5 times of a column volume;

6) purifying the exchanged liquid obtained in the step 5) by means of continuous simulated moving bed chromatography, to obtain a purified liquid; conditions of the continuous simulated moving bed chromatography include a feeding concentration of 50%-55%, a temperature of 45° C.-50° C., a water to material ratio of 1.5:1-2:1, and a treatment capacity of 0.035 kg dry basis/L resin/h-0.045 kg dry basis/L resin/h;

7) concentrating and vacuum drying the purified liquid obtained in the step 6), to obtain Stachyose.

In some embodiments, the method for preparing Stachyose can effectively reduce electrically conductive ash content of the Stachyose, and the method for preparing Stachyose is a preparation method of effectively reducing the electrically conductive ash content in the Stachyose.

In some embodiments, a particle size of the wall-broken material in the step 1) is 3 mm to 5 mm.

In some embodiments, conditions of the filter pressuring in the step 2) include: conducting the filter pressing by using a belt pressure filter, with a pedrail mesh number of 60 meshes-80 meshes, a pressure of 0.2 Mpa-0.5 Mpa, and a temperature of not more than 30° C.

In some embodiments, conditions of the decoloring treatment in the step 3) include: conducting the decoloring treatment by using an immobilized carbon column, with a temperature of 50° C.-60° C., and a flow rate per hour of the filtrate of 0.7 times-1 time of the column volume.

In some embodiments, the nanofiltration membrane in the step 4) has a molecular weight cut-off of 300 Da.

In some embodiments, the conditions of the mixed bed ion exchange treatment in the step 5) include: a temperature of 25° C. and a flow rate per hour of the nanofiltration liquid of 2 times of a column volume.

In some embodiments, the treatment capacity of the step 6) is 0.04 kg dry basis/L resin/h.

In some embodiments, conditions of the vacuum drying in the step 7) include: a pressure of −0.09 Mpa to −0.1 Mpa, and a temperature of 65° C.-85° C.

In some embodiments, the filter residues in the step 2) are vacuum dried to obtain a byproduct vegetable protein.

In some embodiments, the conditions of the vacuum drying include: a pressure of −0.09 Mpa to −0.1 Mpa, and a temperature of 60° C.-80° C.

The present disclosure provides a method for preparing Stachyose. The present disclosure uses a nanofiltration membrane to remove salts and a part of monosaccharides in the decolorized liquid, with a desalination rate reaching more than 99.0%. The desalinated material is further treated by the means of mixed bed ion exchange, to further reduce the electric conductivity of the product, with an electric conductivity of the finished product of ≤50%, and an electrically conductive ash content of ≤0.01%, and also, the use of the mixed bed ion exchange treatment can reduce greatly the degradation of Stachyose during the ion exchange treatment and keep the purity of the Stachyose not to be reduced. The continuous simulated moving bed chromatographic separation is used to increase the purity of the product to more than 98%, reduce the contents of sucrose and other monosaccharides (glucose, fructose), and greatly improve the quality of the product, so that the product can be applied to low-sugar or low-glycemic index products. At the vacuum drying condition, the drying temperature of the material may be reduced, and the stability of Stachyose can be efficiently kept. Finally, a low-salt, low-conductivity and high-purity Stachyose is obtained.

Advantageous Effects of the Disclosure

The Stachyose prepared by using the preparation method provided by the present disclosure has an electric conductivity of 37 μs/cm-41 μs/cm, an electrically conductive ash content of 0.0091%-0.0094% and a purity of 98.92%-99.0%.

DESCRIPTION OF THE TERMS

In the present application, the *Stachys affinis* for extracting Stachyose refers to tubers of the *Stachys affinis.*

In the present application, the mixed bed ion exchange treatment refers to a treatment using a mixed bed ion exchange resin. The mixed bed ion exchange resin refers to a resin containing both an anion exchange resin and a cation exchange resin. The use of the mixed bed ion exchange treatment can remove cation and anion ions in a solution simultaneously.

In the present application, the continuous simulated moving bed chromatographic purification refers to a treatment using simulated moving bed chromatography. In the simulated moving bed technology, a feeding inlet, a solvent or eluent inlet, and locations of exports for desired and undesired products, rather than a bed, are continuously moved, giving the impression that the bed is moved, solid particles continuously flow, and a liquid continuously flows in a direction opposite to that of the solid particles. The continuous simulated moving bed chromatography used in the present application is, for example, any of simulated moving bed chromatography technologies described in the following document, Lin Bingchang, Simulated Moving Bed Chromatography Technology [M], Chemical Industry Press, 2008.

In the present application, the unit "1 kg dry basis/L resin/h" means that a solution containing 1 kg dry basis is treated per liter resin per hour.

In the present application, the "electrically conductive ash content" refers to the weight percentage of substances remained after Stachyose is burnt to completely remove organic substances, relative to the sample.

In the present application, the detection standards for the purity and electrically conductive ash content of the Stachyose refer to QB/T4260-2018; the detection of the conductivity detection refers to GB/T35887-2018; the detection of the chrominance refers to the standard GB/T20881.4-2021; the detection of the light transmittance refers to GB/T20881-2017.

ILLUSTRATIONS TO THE DRAWINGS

The drawings are illustrated here to provide further understandings to the present application and constitute a part of the present application. The schematic examples of the present disclosure and illustrations thereof are used for explaining the present disclosure, but not for limiting the present disclosure. In the following drawings:

FIG. 1 is a flow diagram of the preparation of Stachyose in some embodiments of the present disclosure.

DETAILED DESCRIPTION OF THE INVENTION

References will now be made in detail to specific embodiments of the present disclosure. Examples of the specific embodiments are shown in the drawings. While these specific embodiments describe the present disclosure, it should be recognized that it is not intended to limit the present disclosure to these specific embodiments. In contrast, these embodiments are intended to cover alternative, modified and equivalent embodiments that are included within the inventive spirit and scope as defined by the claims. In the following descriptions, numerous specific details are elaborated to provide thorough understandings to the present disclosure. The present disclosure may be implemented without some or all of these specific details. In other instances, in order not to unnecessarily obscure the present disclosure, well known process operations are not described in detail.

The disclosure provides a method for preparing Stachyose, comprising the following steps:

1) breaking walls of *Stachys affinis*, to obtain a wall-broken material;
2) subjecting the wall-broken material obtained in the step 1) to filter pressing, to obtain a filtrate and filter residues;
3) subjecting the filtrate obtained in the step 2) to a decoloring treatment, to obtain a decolorized liquid;
4) subjecting the decolorized liquid obtained in the step 3) to a nanofiltration membrane filtration, to obtain a nanofiltration liquid;
   conditions of the nanofiltration membrane filtration include: a molecular weight cut-off of the nanofiltration membrane of 100 Da-500 Da, a temperature of 30° C.-40° C., and a pressure of 0.35 Mpa-1 Mpa;
5) subjecting the nanofiltration liquid obtained in the step 4) to a mixed bed ion exchange treatment, to obtain an exchanged liquid;
   conditions of the mixed bed ion exchange treatment include: a temperature of 20° C.-30° C., and a flow rate per hour of the nanofiltration liquid of 1.5 times-2.5 times of a column volume;
6) purifying the exchanged liquid obtained in the step 5) by means of continuous simulated moving bed chromatography, to obtain a purified liquid; conditions of the continuous simulated moving bed chromatography include a feeding concentration of 50%-55%, a temperature of 45° C.-50° C., a water to material ratio of 1.5:1-2:1, and a treatment capacity of 0.035 kg dry basis/L resin/h-0.045 kg dry basis/L resin/h;
7) concentrating and vacuum drying the purified liquid obtained in the step 6), to obtain stachyose.

The present disclosure breaks walls of *Stachys affinis*, to obtain a wall-broken material.

In the present disclosure, the *Stachys affinis* is preferably fresh *Stachys affinis*, which contains 75%-80% of water, 17%-20% of saccharides, 2.5%-5.5% of proteins and ≤0.3% of fat, but free of cellulose and lignin. According to the present disclosure, preferably, after the *Stachys affinis* is cleaned, it is subjected to a wall breaking pretreatment with a hammer-type wall breaking machine, and a screen having a pore size of 4 mm-6 mm is selected as the used wall breaking screen, to control the size of the wall-broken material to be from 3 mm to 5 mm. The size of the wall-broken material affects belt filter pressing effects. A too large size will cause the belt squeeze to have a low juice yield and a high water content in filter residues, and a too low size will result in a reduced quality of the filtrate and too much filter residues.

According to the present disclosure, the obtained wall-broken material is subjected to the filter pressing to obtain a filtrate and filter residues. In the present disclosure, the conditions of the filter pressing preferably include: conducting the filter pressing by using a belt pressure filter, with a pedrail mesh number of 60 meshes-80 meshes, a pressure of 0.2 Mpa-0.5 Mpa, and a temperature of not more than 30° C. In the present disclosure, the filter residues are preferably vacuum dried to obtain a byproduct vegetable protein, and the conditions of the vacuum drying preferably include: a pressure of −0.09 Mpa to −0.1 Mpa, and a temperature of 60° C. to 80° C.

According to the present disclosure, the obtained filtrate is decolorized to obtain decolorized liquid. In the present disclosure, the conditions of the decoloring treatment preferably include: conducting the decoloring treatment by using an immobilized carbon column, with a temperature of 50° C.-60° C., and a flow rate per hour of the filtrate of 0.7 times-1 time of the column volume.

According to the present disclosure, the obtained decolorized liquid is subjected to a nanofiltration membrane filtration, to obtain a nanofiltration liquid; the conditions of the nanofiltration membrane filtration preferably include: a molecular weight cut-off of the nanofiltration membrane of 100 Da to 500 Da, a temperature of 30° C. to 40° C., and a pressure of 0.35 Mpa to 1 Mpa. In the present disclosure, the nanofiltration membrane preferably has a molecular weight cut-off of 300 Da. In the present disclosure, the nanofiltration membrane is adopted to remove salts and a part of monosaccharides in the decolorized liquid, with a desalination rate reaching more than 99.0%.

According to the present disclosure, the obtained nanofiltration liquid is subjected to a mixed bed ion exchange treatment, to obtain an exchanged liquid; the conditions of the mixed bed ion exchange treatment include: a temperature of 20° C. to 30° C., and a flow rate per hour of the nanofiltration liquid of 1.5 times to 2.5 times of a column volume. In the present disclosure, the conditions of the mixed bed ion exchange treatment preferably include: a temperature of 25° C., and a flow rate per hour of the nanofiltration liquid of 2.0 times of a column volume. The mixed bed ion exchange treatment is used to reduce the electric conductivity of the product, with an electric conductivity of the finished product of ≤50%, and an electrically conductive ash content of ≤0.01%, and also, the use of the mixed bed ion exchange treatment can greatly reduce the degradation of Stachyose during the ion exchange treatment and keep the purity of the Stachyose not to be reduced.

According to the present disclosure, the obtained exchanged liquid is purified by means of continuous simulated moving bed chromatography, to obtain a purified liquid; the conditions of the continuous simulated moving bed chromatography include a feeding concentration of 50% to 55%, a temperature of 45° C. to 50° C., a water to material ratio of 1.5:1 to 2:1, and a treatment capacity of 0.035 kg dry basis/L resin/h to 0.045 kg dry basis/L resin/h. In the present disclosure, the treatment capacity is preferably 0.04 kg dry basis/L resin/h. The continuous simulated moving bed chromatographic separation is used to increase the purity of the product to more than 98%, reduce the contents of sucrose and other monosaccharides (glucose, fructose), and greatly improve the quality of the product quality, so that the product can be applied to low-sugar or low-glycemic index products.

According to the present disclosure, the obtained purified liquid is concentrated and vacuum dried, to obtain Stachyose. In the present disclosure, the conditions of the vacuum drying include: a pressure of −0.09 Mpa to −0.1 Mpa, and a temperature of 65° C. to 85° C. According to the present disclosure, a vacuum belt dryer is preferably used to vacuum dry the product. At the vacuum conditions, the drying temperature of the material may be reduced, and the stability of the Stachyose can be efficiently kept. The present disclosure does not specially limit the conditions of the concentrating, and routine conditions may be used.

The concentrations mentioned in the present disclosure each are mass concentrations.

FIG. 1 shows a flow chart of a method for preparing Stachyose according to some embodiments of the present application. As shown in FIG. 1, the method for preparing Stachyose comprises:

(1) providing *Stachys affinis;*

(2) cleaning the *Stachys affinis;*

(3) treatment with hammer-type wall breaking technology;

(4) treatment with belt squeeze technology;

(5) collecting filter residues and a filtrate; after vacuum belt drying the filter residues, obtaining a feed protein;

(6) decoloring the filtrate with an immobilized carbon column;

(7) nanofiltration desalinating treatment;

(8) mixed bed desalinating treatment;

(9) chromatographic purification treatment.

In order to further illustrate the present disclosure, the following examples are combined to describe the present disclosure in detail, but they should not be construed as limiting the protection scope of the disclosure.

Example 1

1. Fresh *Stachys affinis* was cleaned and broken by using a hammer-type wall breaking machine, wherein the pore size of a wall breaking screen was 5 mm, to control the size of the wall-broken material to be about 5 mm;
2. a belt pressure filter was used to conduct a filter pressing treatment, with a pedrail mesh number of 80 meshes, a filter pressing pressure of 0.2 Mpa-0.5 Mpa, and a material temperature of 25° C.;
3. the filter residues obtained by the belt pressure filter was dried by using a low-temperature vacuum belt dryer to obtain a byproduct vegetable protein, with a vacuum degree of −0.01 Mpa, a first-region drying temperature of 75° C., a second-region drying temperature of 65° C., and a cooling temperature of 30° C.;
4. the filtrate was decolorized by using an immobilized carbon column, with a decolonization temperature of 55° C., and a material flow rate per hour of 0.8 times of the column volume;
5. after the decolorization of the filtrate, it was desalinized by using a nanofiltration membrane, with a membrane molecular weight cut-off of 300 Da, a working temperature of 35° C., and a working pressure of 0.5 Mpa-0.6 Mpa;
6. after the nanofiltration of the filtrate, it was subjected to a mixed bed ion exchange treatment, with a material temperature of 25° C., and a material flow rate per hour of 2.0 times of a column volume;
7. the material was purified by a continuous simulated moving bed chromatography, with a feeding concentration of 50%, a working temperature of 45° C., a water to material ratio of 1.5:1, and a treatment capacity of 0.040 kg dry basis/L resin/h;
8. after the continuous simulated moving bed chromatographic purification, the material was concentrated and vacuum dried, with drying conditions: a vacuum degree of −0.1 MPa, a first-region drying temperature of 80° C., and a second-region drying temperature of 70° C.

According to the above operation steps, the results are shown below:

(1) After the wall breaking, the belt filter pressing, the material was detected to obtain the following items:

a juice yield: 90.97%, a solid content of the filtrate: 17.50%, a purity of stachyose in the filtrate: 81.36%, an electrically conductive ash content of the filtrate: 0.94%, an electric conductivity: ≥10000 μs/cm, a light transmittance of the material: 48.5%, a chrominance: 415.62, and a residue yield: 9.03%.

(2) The obtained filter residues were dried by a low-temperature vacuum belt dryer, and 31.79 kg of a byproduct vegetable protein could be produced from each ton of raw materials; after detections, the purity of the protein was 81.64%, and 18.36% of the rest predominantly were sugar and traces of fat.

(3) After the decolorizing treatment with an immobilized carbon column, the material had a light transmittance of 85.6%, a chrominance of 87.41, and a purity of stachyose of 81.14%.

(4) After the desalination treatment with a nanofiltration membrane, the material had a light transmittance of 92.3%, a chrominance of 43.51, an electric conductivity of 261 μs/cm, an electrically conductive ash content of 0.081%, and a purity of stachyose of 82.17%.

(5) After the desalination treatment with a mixed bed ion exchange, the material had a light transmittance of 99.1%, a chrominance of 8.07, an electric conductivity of 38 μs/cm, an electrically conductive ash content of 0.0093% and a purity of stachyose of 82.23%.

(6) After the continuous simulated moving bed chromatographic purification and concentrating, the material had a light transmittance of 99.0%, a chrominance of 8.10, an electric conductivity of 38 μs/cm, an electrically conductive ash content of 0.0093%, and a purity of stachyose of 98.73%.

(7) After the low-temperature vacuum drying, a stachyose finished product was obtained, with a purity of the finished product of 98.67%, an electrically conductive ash content of 0.0091%, an electric conductivity of 37 μs/cm, a chrominance of 8.00, and a light transmittance of 99.0%.

Example 2

1. Fresh *Stachys affinis* was cleaned and broken by using a hammer-type wall breaking machine, wherein the pore size of a wall breaking screen was 4 mm, to control the size of the wall-broken material to be about 4 mm;
2. a belt pressure filter was used to conduct a filter pressing treatment, with a pedrail mesh number of 70 meshes, a filter pressing pressure of 0.2 Mpa-0.5 Mpa, and a material temperature of 25° C.;
3. the filter residues obtained by the belt pressure filter was dried by using a low-temperature vacuum belt dryer to obtain a byproduct vegetable protein, with a vacuum degree of −0.01 Mpa, a first-region drying temperature of 75° C., a second-region drying temperature of 60° C., and a cooling temperature of 30° C.;
4. the filtrate was decolorized by using an immobilized carbon column, with a decolonization temperature of 60° C., and a material flow rate per hour of 1.0 time of the column volume;
5. after the decolorization of the filtrate, it was desalinized by using a nanofiltration membrane, with a membrane molecular weight cut-off of 300 Da, a working temperature of 30° C., and a working pressure of 0.6 Mpa-0.7 Mpa;
6. after the nanofiltration of the filtrate, it was subjected to a mixed bed ion exchange treatment, with a material temperature of 30° C., and a material flow rate per hour of 2.5 times of a column volume;
7. the material was purified by a continuous simulated moving bed chromatography, with a feeding concentration of 55%, a working temperature of 50° C., a water to material ratio of 2.0:1, and a treatment capacity of 0.040 kg dry basis/L resin/h;
8. after the continuous simulated moving bed chromatographic purification, the material was concentrated and vacuum dried, with drying conditions: a vacuum degree of −0.1 MPa, a first-region drying temperature of 80° C., and a second-region drying temperature of 65° C.

According to the above operation steps, the results are shown below:

(1) After the wall breaking, the belt filter pressing, the material was detected to obtain the following items:

a juice yield: 91.31%, a solid content of the filtrate: 17.25%, a purity of stachyose in the filtrate: 82.31%, an electrically conductive ash content of the filtrate: 0.97%, an electric conductivity: ≥10000 μs/cm, a light transmittance of the material: 45.6%, a chrominance: 478.62, and a residue yield: 8.69%.

(2) The obtained filter residues were dried by a low-temperature vacuum belt dryer, and 30.55 kg of a byproduct vegetable protein could be produced from each ton of raw materials; after detections, the purity of the protein was 78.45%, and 21.55% of the rest predominantly were sugar and traces of fat.

(3) After the decolorizing treatment with an immobilized carbon column, the material had a light transmittance of 86.2%, a chrominance of 78.24, and a purity of stachyose of 81.93%.

(4) After the desalination treatment with a nanofiltration membrane, the material had a light transmittance of 93.5%, a chrominance of 38.69, an electric conductivity of 261 μs/cm, an electrically conductive ash content of 0.088%, and a purity of stachyose of 82.34%.

(5) After the desalination treatment with a mixed bed ion exchange, the material had a light transmittance of 99.3%, a chrominance of 7.01, an electric conductivity of 41 μs/cm, an electrically conductive ash content of 0.0094% and a purity of stachyose of 82.23%.

(6) After the continuous simulated moving bed chromatographic purification and concentrating, the material had a light transmittance of 99.2%, a chrominance of 7.20, an electric conductivity of 41 μs/cm, an electrically conductive ash content of 0.0094%, and a purity of stachyose of 98.95%.

(7) After the low-temperature vacuum drying, a stachyose finished product was obtained, with a purity of the finished product of 98.92%, an electrically conductive ash content of 0.0094%, an electric conductivity of 41 μs/cm, a chrominance of 7.20, and a light transmittance of 99.2%.

Comparative Examples 1 to 2

Comparative Examples 1-2 differed from Example 1 in the parameter settings of the continuous simulated moving bed chromatography. The differences in the continuous simulated moving bed parameter settings between Comparative Examples 1-2 and Example 1 were shown below:

| | Example 1 | Comparative Example 1 | Comparative Example 2 |
|---|---|---|---|
| Feeding concentration | 50% | 45% | 60% |
| Temperature | 45° C. | 40° C. | 60° C. |
| Water/material ratio | 1.5:1 | 1:1 | 2.5:1 |

As mentioned above, after the product purified by continuous simulated moving bed chromatography in Example 1 was vacuum dried at low temperatures, a stachyose finished product was obtained, with a purity of the finished product of 98.67%, an electrically conductive ash content of 0.0091%, an electric conductivity of 37 μs/cm, a chrominance of 8.00, and a light transmittance of 99.0%.

After the product purified by continuous simulated moving bed chromatography in Comparative Example 1 was vacuum dried at low temperatures, a stachyose finished product was obtained, with a purity of the finished product of 94.37%, an electrically conductive ash content of 0.0101%, an electric conductivity of 53 μs/cm, a chrominance of 10.34, and a light transmittance of 99.0%. Comparative Example 1 was inferior to Example 1.

After the product purified by continuous simulated moving bed chromatography in Comparative Example 2 was vacuum dried at low temperatures, a stachyose finished product was obtained, with a purity of the finished product of 97.48%, an electrically conductive ash content of 0.0099%, an electric conductivity of 47 μs/cm, a chrominance of 9.62, and a light transmittance of 98.9%. Comparative example 2 was inferior to Example 1.

In Comparative Example 1, the feeding concentration, temperature and water to material ratio of the continuous simulated moving bed chromatography were lower than the ranges in the technical solution of the present disclosure (that is, the feeding concentration: 50-55%, the temperature: 45-50° C., and the water to material ratio: 1.5-2:1), and the stachyose product obtained in Comparative Example 1 was inferior to that of Example 1 in terms of the property parameters like purity, electric conductivity, etc.

In Comparative Example 2, the feeding concentration, temperature and water to material ratio of the continuous simulated moving bed chromatography were higher than the ranges in the technical solution of the present disclosure (that is, the feeding concentration: 50-55%, the temperature: 45-50° C., and the water to material ratio: 1.5-2:1), and the stachyose product obtained in Comparative Example 2 was inferior to that of Example 1 in terms of the property parameters like purity, electric conductivity, etc.

As can be seen from this, Examples 1-2 in the present disclosure use specific continuous simulated moving bed chromatographic parameters to effectively improve the quality of the stachyose product, particularly to reduce the electrically conductive ash content of the stachyose, and they achieve significant unexpected technical effects.

While the present application has been described with reference to preferred examples, without departing from the scope of the present application, various modifications may be made and equivalents may be used to replace elements therein. Especially, as long as there is no structural conflict, the respective technical features mentioned in the respective examples may be combined in any way. The present application is not be limited to the specific examples disclosed herein, but includes all technical solutions falling within the scope of the claims.

The invention claimed is:

1. A method for preparing Stachyose, comprising the following steps:

1) breaking walls of *Stachys affinis* to obtain a wall-broken material;
2) subjecting the wall-broken material obtained in step 1) to filter pressing to obtain a filtrate and filter residues;
3) subjecting the filtrate obtained in step 2) to a decoloring treatment to obtain a decolorized liquid;
4) subjecting the decolorized liquid obtained in step 3) to a nanofiltration membrane filtration to obtain a nanofiltration liquid, wherein conditions of the nanofiltration membrane filtration comprise: a molecular weight cut-off of the nanofiltration membrane of 100 Da to 500 Da, a temperature of 30° C. to 40° C., and a pressure of 0.35 Mpa to 1 Mpa;
5) subjecting the nanofiltration liquid obtained in step 4) to a mixed bed ion exchange treatment to obtain an exchanged liquid, wherein conditions of the mixed bed ion exchange treatment comprise: a temperature of 20° C. to 30° C., and a flow rate per hour of the nanofiltration liquid of 1.5 times to 2.5 times of a column volume;
6) purifying the exchanged liquid obtained in step 5) by means of continuous simulated moving bed chromatography to obtain a purified liquid, wherein conditions of the continuous simulated moving bed chromatography comprise a feeding concentration of 50% to 55%, a temperature of 45° C. to 50° C., a water to material ratio of 1.5:1 to 2:1, and a treatment capacity of 0.035 kg dry basis/L resin/h to 0.045 kg dry basis/L resin/h; and
7) concentrating and vacuum drying the purified liquid obtained in step 6) to obtain Stachyose.

2. The method according to claim 1, wherein the particle size of the wall-broken material in step 1) is 3 mm to 5 mm.

3. The method according to claim 1, wherein conditions of the filter pressuring in step 2) comprise: conducting the filter pressing by using a belt pressure filter with a pedrail mesh number of 60 meshes-80 meshes, a pressure of 0.2 Mpa-0.5 Mpa, and a temperature of not more than 30° C.

4. The method according to claim 1, wherein conditions of the decoloring treatment in step 3) comprise: conducting the decoloring treatment by using an immobilized carbon column with a temperature of 50° C.-60° C. and a flow rate per hour of the filtrate of 0.7 times-1 time of the column volume.

5. The method according to claim 1, wherein the nanofiltration membrane in step 4) has a molecular weight cut-off of 300 Da.

6. The method according to claim 1, wherein conditions of the mixed bed ion exchange treatment in step 5) comprise: a temperature of 25° C. and a flow rate per hour of the nanofiltration liquid of 2 times of the column volume.

7. The method according to claim 1, wherein the treatment capacity of step 6) is 0.04 kg dry basis/L resin/h.

8. The method according to claim 1, wherein conditions of the vacuum drying in step 7) comprise: a pressure of −0.09 Mpa to −0.1 Mpa and a temperature of 65° C. to 85° C.

9. The method according to claim 1, wherein the filter residues in step 2) are vacuum dried to obtain a byproduct vegetable protein.

10. The method according to claim 9, wherein conditions of the vacuum drying comprise: a pressure of −0.09 Mpa to −0.1 Mpa and a temperature of 60° C. to 80° C.

* * * * *